United States Patent [19]

Roberts

[11] 4,124,030
[45] Nov. 7, 1978

[54] ELECTRO-THERAPEUTIC FARADIC CURRENT GENERATOR

[76] Inventor: Wallace A. Roberts, 88 N. Main St., Bellingham, Mass. 02019

[21] Appl. No.: 756,781

[22] Filed: Jan. 5, 1977

[51] Int. Cl.² ............................................. A61N 1/36
[52] U.S. Cl. .................................................... 128/422
[58] Field of Search ........... 128/419 R, 420 A, 420 R, 128/421, 422, 423 R

[56] References Cited

U.S. PATENT DOCUMENTS

| | | | |
|---|---|---|---|
| 3,108,597 | 10/1963 | Moss et al. ............................ 128/422 |
| 3,109,430 | 11/1963 | Tischler ................................ 128/422 |
| 3,387,147 | 6/1968 | Radwan ............................ 128/422 X |
| 3,766,413 | 10/1973 | Berkovits ........................ 128/422 X |
| 3,794,022 | 2/1974 | Nawracaj et al. ........... 128/420 A X |
| 3,797,500 | 3/1974 | Porter ................................... 128/422 |
| 3,908,669 | 9/1975 | Man et al. ............................. 128/422 |
| 3,911,930 | 10/1975 | Hagfors et al. .................. 128/422 X |
| 3,958,577 | 5/1975 | Rodler .............................. 128/420 A |

*Primary Examiner*—Wm. E. Kamm
*Attorney, Agent, or Firm*—William Nitkin

[57] ABSTRACT

Therapeutic faradic current generators are used for stimulation of muscles and nerves of a body. Disclosed is such a generator in one embodiment having a unijunction transistor relaxation oscillator that feeds a Schmitt trigger, the output of which gates a power oscillator. The power oscillator drives a pair of electrodes that are put in contact with the skin.

1 Claim, 1 Drawing Figure

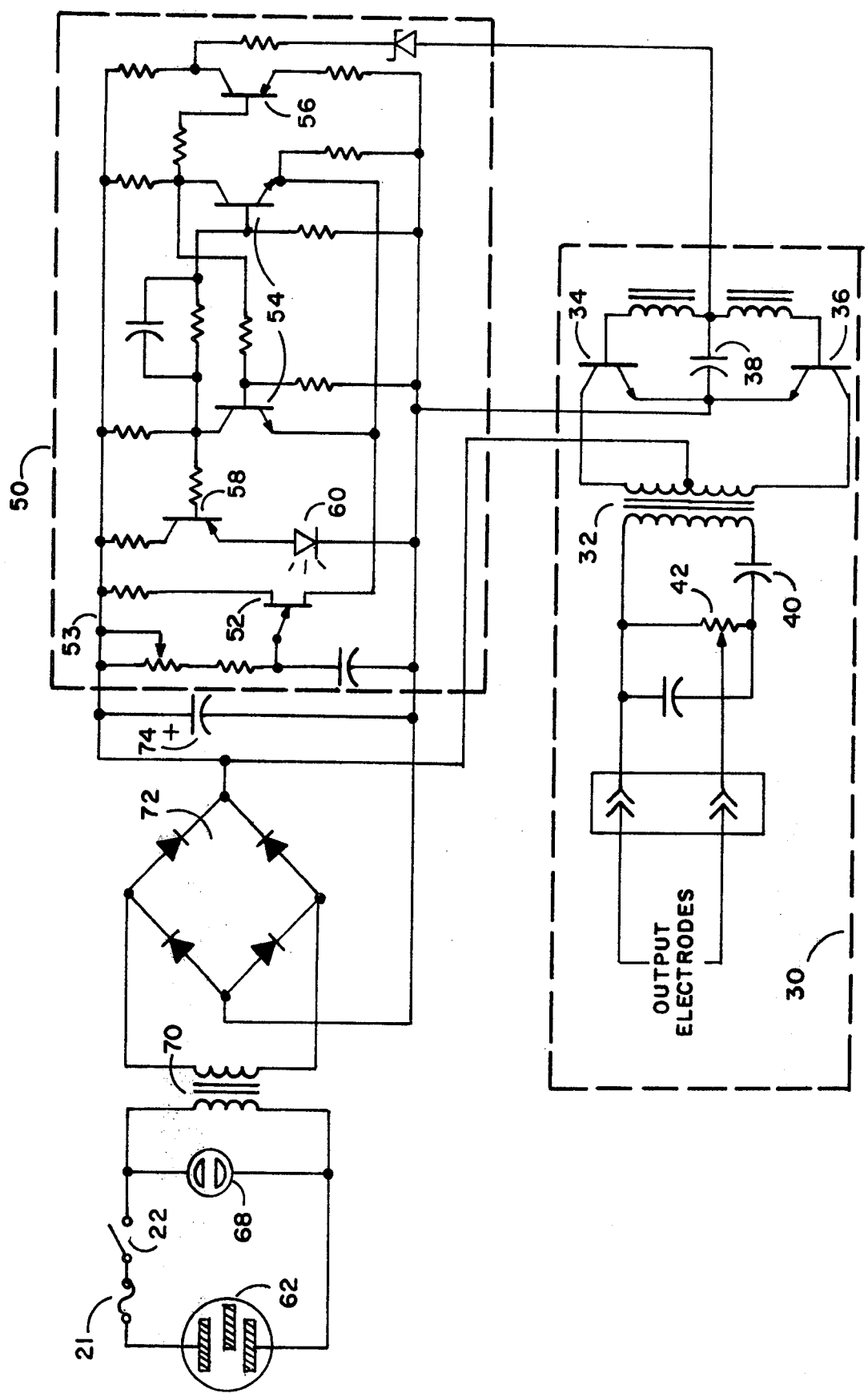

ELECTRO-THERAPEUTIC FARADIC CURRENT GENERATOR

BACKGROUND OF THE INVENTION

The device of this invention is an improved electro-therapeutic faradic current generator for use in the treatment of "cellulite", (which term is defined below), poor circulation and poor muscle tone. Faradic current generators have long been in use. Originally such generators consisted of an induction coil producing a rapidly alternating current. These induction coils consisted of two parallel coils: a primary coil and a secondary coil employed for the production of currents by mutual induction. A rapidly interrupted direct current would be supplied to the primary coil which would induce alternating currents in the secondary coil. The output of the secondary coil would be applied to the skin by electrodes. This direct application of current along with its potential fluctuations could at times cause unpleasant shocks in subjects. Over the years the art developed so that the faradic currents were produced by a type of inverted induction coil sometimes called a converter or a transformer in order to achieve a higher degree of control over the process. Still a malfunction could expose the subject to unexpected shocks as the current is basically received in line from the output of the transformer.

SUMMARY

The present invention relates to faradic current generators for therapeutic muscle and nerve stimulation and more particularly relates to transistorized circuitry which produces successive bursts of alternating current in an output transformer. The invention further relates to utilization of dual circuitry, one circuit constant and one circuit variable, accomplished by integrated circuits, to produce an interferential current, the integrated circuits producing a variable frequency faradic wave amplification and oscillation for a multiple output transformer.

It is an object of this invention to provide an improved faradic current generator which does not expose the subject to whom the electrodes are applied to the line current and which will safely provide for improved control over the process. Disclosed herein is a unit for muscle stimulation, especially in the legs for treatment of "cellulite", which term is herein used to refer to deposits of fatty tissue under the skin which cause unsightly bumps. The contraction of the muscles in the area of the cellulite causes a rearrangement of these fatty deposits thereby having a smoothing effect on the skin.

The aforementioned objects will become clearer with reference to the following drawing and Description of the Preferred Embodiment.

BRIEF DESCRIPTION OF THE DRAWING

The FIGURE is a schematic of a preferred embodiment of the invention.

DESCRIPTION OF THE PREFERRED EMBODIMENT

In operation of a faradic generator in accordance with this invention, the generator is connected to a pair of the electrode paddles. These electrodes are applied to subject's body with reference to particular muscles and the unit produces a variable rate faradic current which stimulates the muscle in the vicinity of the electrodes to contract. The current is generated in bursts having a repetition rate adjustable over a range from 0.5 to 4 seconds. Each burst of current is alternating current, the most desirable frequency which depends in part on the type of muscle to be stimulated; the frequency also affects the consequent sensation felt by the subject. It has been found that 7500 cycles per second is a desirable frequency for use on facial muscles. Frequencies can range from 1,000 to 25,000 cycles per second and at the low end of the range the sensation can be painful while above the 25,0000 cycles per second the muscles fail to respond.

The FIGURE illustrates a schematic diagram of an embodiment of a faradic current generator in accordance with the present invention and embodying one of the improvements disclosed. The power oscillator section 30 is seen whose main component is transformer 32 which is used in conjunction with first transistor 34 and second transistor 36 and capacitor 38. First and second transistors 34 and 36 oscillate at a frequency determined by the physical construction of transformer 32 and by the capacitance of capacitor 38. The output of transformer 32 passes through a 0.5 microfarad capacitor 40 to a 2.5 K ohm potentiometer 42. Potentiometer 42 is the output intensity control adjusted by knob 26 in FIG. 1 and is adjustable between 0 and 100 volts peak to peak of faradic voltage. The output then travels to output plug 22 seen in FIG. 1 into which is connected the output electrodes. The electrodes can be constructed of stainless steel or equivalent material and have a disk-shaped face, about 1½ inches in diameter, for contacting the skin. The power oscillator section 30 is gated on at a variable rate by pulse section 50. Within pulse section 50 is a unijunction transistor oscillator 52 which may be a 2N4871 transistor or equivalent which fires between 0.5 and 4 second intervals. A 100 K ohm potentiometer 53 controls the firing rate and is adjusted by rate adjustment knob 24 on the face of the unit. The output of transistor 52 enters a Schmitt triggger 54 comprised of two transistors. Each time the unijunction transistor 52 fires a pulse, the two transistors in the Schmitt trigger alternate state. The output of one of the transistors in the Schmitt trigger 54 activates buffer transistor 56 which controls the output of the power oscillator section 30. The second transistor in the Schmitt trigger 54 activates transistor 58 which controls light-emitting diode 60 which is seen as output indicator light 28 on the front panel of casing 30 in FIG. 1. Light-emitting diode 60 lights when a pulse is fired activating the power oscillating section which causes galvanic current at the electrodes. The unit receives power from house current into AC receptacle 62 through a ½ amp fuse 21 in line with off/on switch 22. The power when on causes bulb 68 to light indicator 12. The power enters transformer 70 which has an output of 12.6 volts which passes to a bridge rectifier 72 whose output is filtered by an electrolytic capacitor 74 and applied to the circuit.

Although the present invention has been described with reference to particular embodiments, it will be apparent to those skilled in the art that variations and modifications can be substituted therefor without departing from the principles and spirit of the invention.

I claim:
1. A faradic current generator, comprising
   a single transistor relaxation oscillator having an adjustable firing rate;

a pair of transistors connected to operate as a Schmitt trigger, with two opposite-phased outputs and interconnected emitters, and to receive, at the interconnection of the emitters, the oscillator's output;

a single transistor buffer amplifier, having its input connected to one end of the Schmitt trigger outputs;

a second single transistor amplifier, having its input connected to the other one of the Schmitt trigger outputs, and having a light-emitting diode in the output thereof;

a power oscillator, having two transistors connected in a push-pull configuration, and connected to the output of the buffer amplifier in such a way that a pulse from the buffer amplifier triggers an alternating current burst in the output of the power oscillator for approximately the duration of the pulse; and means for connecting electrodes to the output of the power oscillator.

* * * * *